United States Patent [19]

Yamada

[11] Patent Number: 4,761,719
[45] Date of Patent: Aug. 2, 1988

[54] DENTAL LIGHTING DEVICE

[75] Inventor: Kosaku Yamada, Ikoma, Japan

[73] Assignee: Kabushiki Kaisha Morita Seisakusho, Kyoto, Japan

[21] Appl. No.: 15,971

[22] Filed: Feb. 18, 1987

[30] Foreign Application Priority Data

Feb. 19, 1986 [JP] Japan .................................. 61-23676
Jan. 13, 1987 [JP] Japan .................................. 62-7115

[51] Int. Cl.⁴ ............................................ F21V 33/00
[52] U.S. Cl. .................................... 362/135; 362/142; 362/804
[58] Field of Search ............... 362/804, 135, 138, 139, 362/280, 282, 142, 319, 322, 323, 277; 433/29, 30, 31

[56] References Cited

U.S. PATENT DOCUMENTS

| | | | |
|---|---|---|---|
| 2,093,457 | 9/1937 | Kuklin | 362/142 |
| 2,240,785 | 5/1941 | Johnson | 362/144 |
| 2,319,745 | 5/1943 | Napoli | 362/135 |
| 2,587,941 | 3/1952 | Wiedenhoeft | 362/144 |
| 4,212,105 | 7/1980 | Hukuba | 433/30 |
| 4,254,455 | 3/1981 | Neal, Jr. | 362/804 |

FOREIGN PATENT DOCUMENTS

| | | | |
|---|---|---|---|
| 736607 | 9/1932 | France | 362/139 |
| 8201814 | 6/1982 | PCT Int'l Appl. | 362/139 |

Primary Examiner—Ira S. Lazarus
Assistant Examiner—D. M. Cox
Attorney, Agent, or Firm—Koda and Androlia

[57] ABSTRACT

A dental lighting device arranged such that the light from a light source is reflected by a reflection plate and is cast into the inside of the mouth, wherein a mirror member used to look at the inside the mouth is provided in combination with a lighting device component so that the mirror member can take a mirror use posture where the surface of the mirror member is almost perpendicular to the light beam from the reflection plate at least when the mirror member is used. The mirror member of the lighting device can also take a mirror non-use posture where the mirror surface does not intercept the light beam.

8 Claims, 5 Drawing Sheets

DENTAL LIGHTING DEVICE

BACKGROUND OF THE INVENTION

1. Field of the Invention

The present invention relates to a lighting device used to light the inside of the mouth during dental diagnosis and treatment.

2. Prior Art

Generally, a lighting unit for dental diagnosis and treatment has a lighting device at the end of a swivel arm so that the lighting direction from an upper oblique position to the dental chair and the lighting device holding position can be adjusted as desired.

This lighting device is generally called an astral lamp. The reflection plate of the lighting device is curved so that the light is effectively cast to the inside of the mouth during dental diagnosis and treatment. The light source lamp of the lighting device is disposed inside the curved reflection plate surface so that no shadow is generated inside the mouth even when the dentist intercepts a part of the light beam of the lighting device. The front side (patient side) of the light source lamp is covered with a light source cover. Except the light source cover, the front surface of the conventional lighting device is optically open to obtain better lighting efficiency.

Therefore, when the patient wishes to look at a treatment section, for example, a false tooth section, the patient or the dentist (or the dentist's assistant) must hold a hand mirror to look at the inside and vicinity of the patient's mouth. This is inconvenient and troublesome, and takes a long time to adjust the hand mirror surface at the optimum angle, imposing a great burden on the patient and the dentist.

In addition, light must be cast into the mouth of the patient using a lighting device when looking at the inside of the mouth using a mirror. In this case, light must be cast away from the hand mirror. Therefore, the position and the lighting direction of the lighting device must be finely adjusted. Furthermore, when the dentist instructs the patient how to mount false teeth, both hands of the dentist and those of the patient should be left free for higher working efficiency. However, since the patient or the dentist must hold the hand mirror, working efficiency is reduced.

SUMMARY OF THE INVENTION

It is therefore an object of the present invention to provide the first and second configurations so that both hands of the patient and those of the dentist can be left free and so that the patient can easily look at the inside of his mouth using a mirror without holding the mirror while light is cast into the mouth. The first configuration relates to a dental lighting device including a lighting device component composed of a lighting section having a light source and a reflection plate, and a lighting support section which adjustably supports the lighting section, wherein the light from the light source is cast into the mouth of a patient via the reflection plate, the lighting device being characterized in that the device comprises a mirror member in combination with the lighting device component to allow the patient to look at the inside of his mouth so that the mirror member can have a mirror use posture where the surface of the mirror member is almost perpendicular to the light beam from the reflection plate at least when the mirror member is used.

The second configuration relates to a dental lighting device including a lighting device component composed of a lighting section having a light source and a reflection plate, and a lighting support section which adjustably supports the lighting section, wherein the light from the light source is cast into the mouth of a patient via the reflection plate, the lighting device being characterized in that the device comprises a mirror member in combination with the lighting device component to allow the patient to look at the inside of his mouth so that the mirror member can have two switchable postures one of which being a mirror use posture where the surface of the mirror member is almost perpendicular to the light beam from the reflection plate at least when the mirror member is used, and the other being a mirror non-use posture where the surface of the mirror member does not intercept the light beam when the mirror member is not used.

According to the first configuration, the mirror member is mountable on the lighting device having the lighting section and the lighting support section, and the mirror member is held by the lighting device components so that the mirror surface of the mirror member can have the mirror use posture where the mirror surface is almost perpendicular to the light beam from the reflection plate at least when the mirror member is used. Therefore, both hands of the patient and those of the dentist can be left free when the mirror member is used. The relationship between the mirror surface and the light beam is fixed at all times, resulting in easy positional alignment of the lighting device.

According to the second configuration, the mirror member is mounted on the lighting device having the lighting section and the lighting support section and the mirror member is positioned in the lighting area. The mirror member is designed to have two switchable postures: the mirror use posture where the mirror surface is almost perpendicular to the light beam from the reflection plate and the mirror non-use posture where the mirror member does not intercept the light beam, Therefore, the mirror member can be easily set in place and the patient can look at the inside of his mouth by just turning his eyes on the mirror surface when the mirror member is set in place.

The above and other advantages of the present invention will become more apparent in the following description and the accompanying drawings.

BRIEF DESCRIPTION OF THE DRAWINGS

The accompanying drawings show the embodiments of the present invention.

DETAILED DESCRIPTION OF THE INVENTION

Around the dental chair 1, a lighting device 2 is disposed together with an instrument tray (not shown) and an X-ray photographing apparatus (not shown). An example of the lighting device 2 shown in FIG. 4 has a lighting section I at the end of a swivel arm 4 extended from a wall surface 3 so that the lighting direction and the lighting device support position can be set as desired obliquely above the dental chair 1.

Figure 1:
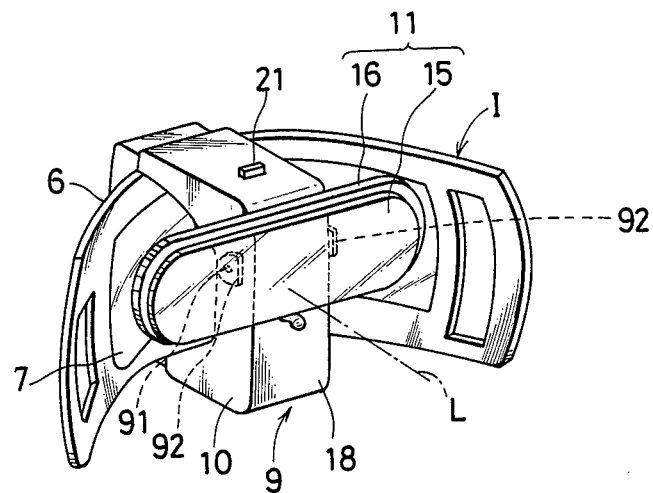
FIG. 1 is an overall perspective view of the first embodiment.
Figure 2:
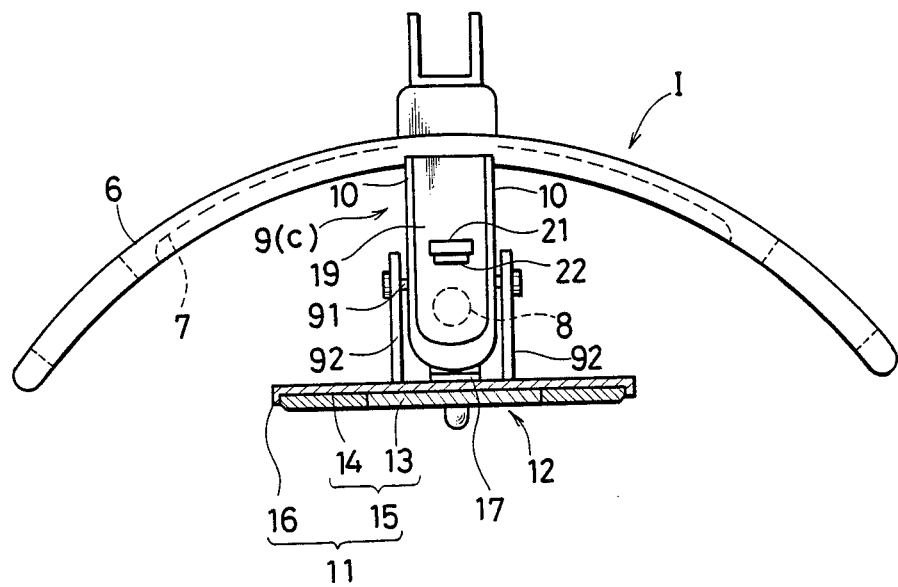
FIG. 2 is a partially sectional plan view of the first embodiment.
Figure 4:
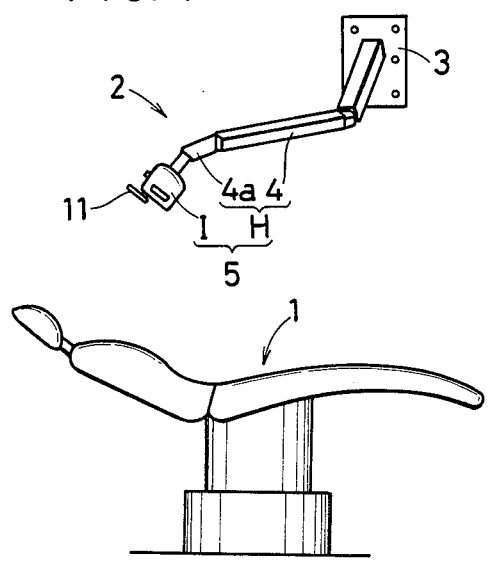
FIG. 4 is a view illustrating the use condition of the first embodiment.

Numeral 5 in FIG. 4 designates a lighting device. As shown in FIG. 2, this lighting device 5 comprises the lighting section I including a frame section 6, a reflection plate 7 fixed inside the frame section 6, a light source lamp 8 disposed close to the focus of the parabola of the reflection plate 7 and a light source cover 9 used to cover the front side (dental chair side) of the light source lamp 8, and a lighting support section H including the swivel arm 4 used to swingably support the lighting section I and a connection arm 4a. The sections I and H compose a lighting device component.

Figure 3:
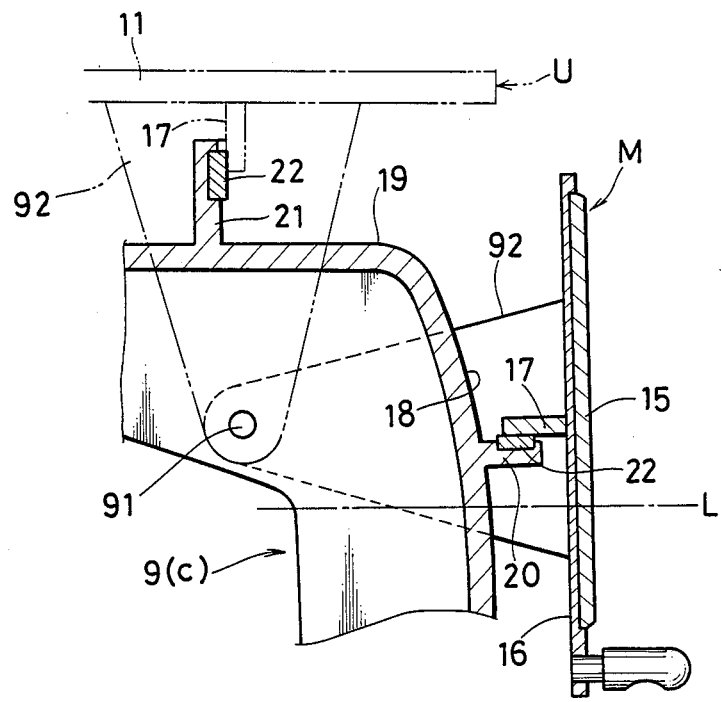
FIG. 3 is a vertical sectional view of the main section of the first embodiment.

A mirror member 11 is swingably supported on the side walls 10 of the light source cover 9 via a shaft 91 and a bracket 92 so that the mirror member 11 can swing up and down. This mirror member 11 comprises a plane mirror 15 and a frame 16 used to support the plane mirror 15. The plane mirror 15 comprises an ordinary mirror 13 disposed at the central section of the mirror surface 12 and semitransparent mirrors 14 disposed at the right and left portions of the mirror surface 12. As shown in FIG. 3, a positioning piece 17 is projected from the rear of the frame 16 to the front of the light source cover 9. The positioning piece 17 is made of magnetic material, such as steel sheet.

To receive the positioning piece 17, receiving sections 20 and 21 are formed on the front 18 and the top 19 of the light source cover 9. The receiving section 20 is disposed on the front 18 of the light source cover 9 so that the receiving section 20 can hold the mirror member 11 in the mirror use posture M where the mirror surface 12 is perpendicular to the optical axis L of the lighting device 5 when the receiving section 20 receives and supports the bottom section of the positioning piece 17 of the mirror member 11. The receiving section 21 is disposed at the top 19 of the light source cover 9 so that the receiving section 21 can hold the mirror member 11 in the mirror non-use posture U where the mirror member 11 is moved to the top 19 of the light source cover 9 and is completely away from the lighting area of the lighting device 5 and the mirror surface 12 is parallel to the optical axis L. Magnets 22 are disposed at the receiving sections 20 and 21. When the positioning piece 17 made of magnetic material is attracted by the magnets 22, the mirror member 11 is securely held in the mirror use posture M or the mirror non-use posture U.

The semitransparent mirrors 14 of this embodiment disposed at the right and left portions of the mirror surface 12 function to dim the light from the reflection plate 7 when the mirror member 11 is held in the mirror use posture M with the lighting device 5 turned on. As a result, the patient is not dazed even when he turns his eyes on the mirror surface 12. In addition, since the greater part of the mirror surface 12 of the mirror member 11 is positioned at the upper half section of the lighting area of the lighting device 5 when the mirror member 11 is held in the mirror use posture M, the patient can look at the inside of his mouth by just turning his eyes on the mirror surface 12. Since his eyes do not meet the light beam, he is not dazed.

Figure 5:
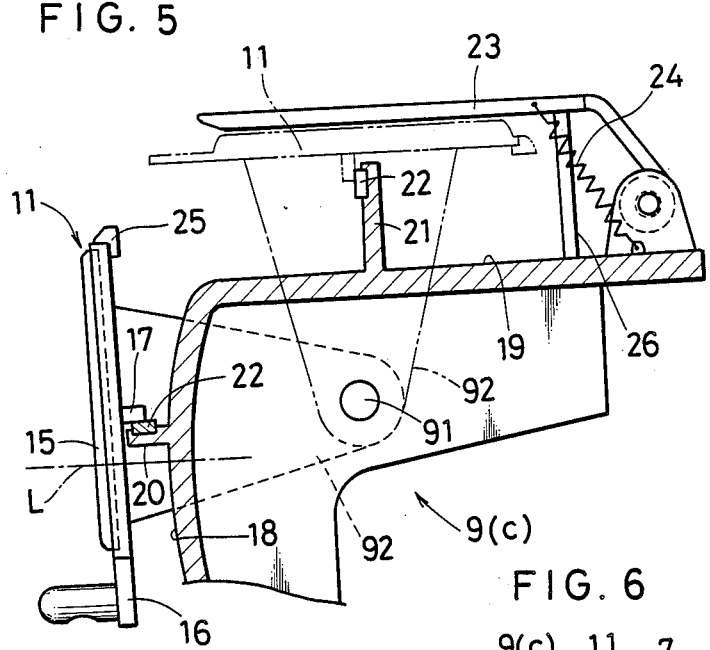
FIG. 5 is a vertical sectional view of the main section of the second embodiment.

FIG. 5 shows the second embodiment of the present invention, a modification of the first embodiment. A cover 23 is swingably supported at the rear section of the top 19 of the light source cover 9. The cover 23 is pulled by a return spring 24 to the top 19 of the light source cover 9. A cam piece 25 is projected at the upper end of the frame 16 of the mirror member 11. When the mirror member 11 is swung up to switch the posture of the mirror member 11, the cam piece 25 contacts the inside of the cover 23 and raises the cover 23 against the force of the return spring 24 to open the cover 23 so that the mirror surface 12 of the plane mirror 15 can be covered with the cover 23 while the mirror member 11 is held in the mirror non-use posture U. Numeral 26 in FIG. 5 designates a spacer which receives the cover 23 so that the cover 23 is parallel to the top 19 of the light source cover 9. The spacer 26 is integrated with and projected from the top 19 of the light source cover 19. The spacer 26 can be projected from the cover 23.

The cover 23 prevents the light of the lighting device disposed on the ceiling from being reflected by the mirror member 11 when the mirror member 11 is held in the mirror non-use posture U during treatment. As a result, the dentist is not adversely affected by light reflection and the mirror surface 12 is kept away from dust.

Figure 6:
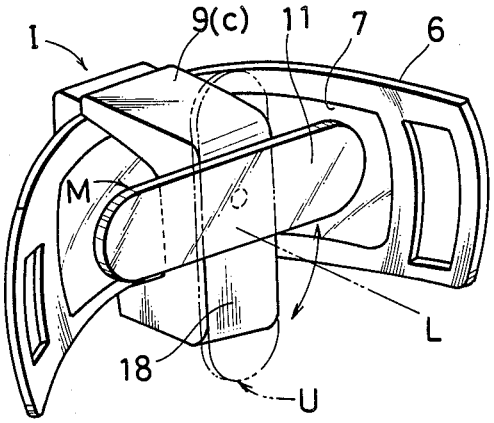
FIG. 6 is a perspective view of the third embodiment.

FIG. 6 shows the third embodiment. With this embodiment, the mirror member 11 is supported on the front 18 of the light source cover 9 so that the mirror member 11 can swing in the plane perpendicular to the optical axis L. In the case of this embodiment, the mirror member 11 is formed so that the mirror member 11 can be held horizontally in the mirror use posture M as indicated by the solid lines and vertically in the mirror non-use posture U along the front wall 18. In the mirror non-use posture, the mirror member 11 scarcely protrudes to the sides of the light source cover 9. Therefore, the light beam is not intercepted by the mirror member 11.

Figure 7:
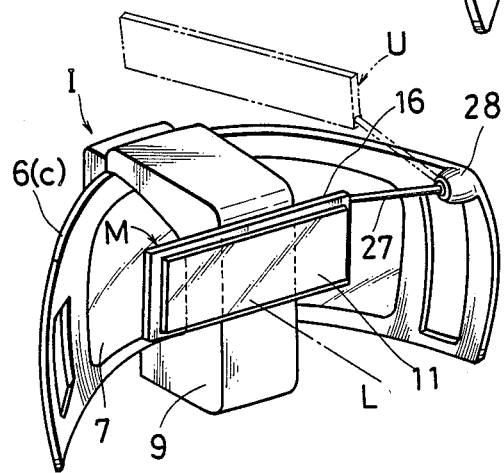
FIG. 7 is a perspective view of the fourth embodiment.

FIG. 7 shows the fourth embodiment. With this embodiment, the mirror member 11 is swingably supported by the frame section 6 of the lighting device 5. More particularly, the support arm 27 extended from the frame 16 of the mirror member 11 is supported by the spherical joint 28 of the frame section 6. By swinging the mirror member 11 around the spherical joint 28, the mirror member 11 can have two switchable postures: the mirror use posture M where the mirror surface 12 of the mirror member 11 is perpendicular to the optical axis L in the lighting area of the lighting device 5 and the mirror non-use posture where the mirror member 11 is moved away from the lighting area of the lighting device 5.

Figure 8:
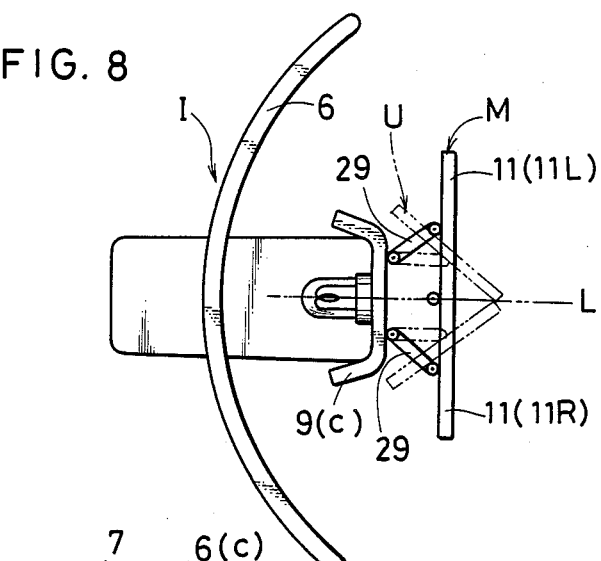
FIG. 8 is a plan view of the main section of the fifth embodiment.

FIG. 8 shows the fifth embodiment. With this embodiment, the mirror member 11 is separated into two folding pieces: a left-half piece 11L and a right-half piece 11R. These pieces are pivotably connected by links 29 and supported on the front wall 18 of the light source cover 9. In the mirror non-use posture U, the mirror member 11 folds, that is, the left-half piece 11L and the right-half piece 11R are moved at the positions indicated by the two-dot chain lines so that they do not extend to the sides of the light source cover 9. In the mirror use posture M, the mirror member 11 has a plane surface.

Figure 9:
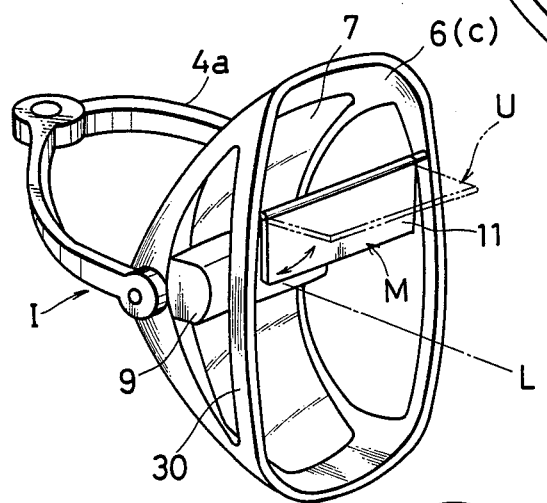
FIG. 9 is a perspective view of the sixth embodiment.
Figure 10:
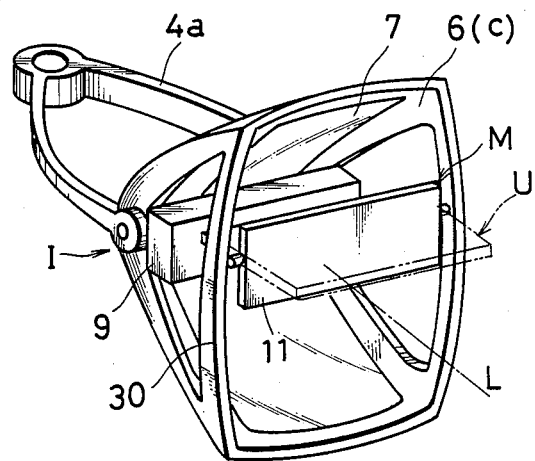
FIG. 10 is a perspective view of the seventh embodiment.

FIGS. 9 and 10 show the embodiments applied to the lighting device 5 having the reflection plate 7 disposed vertically. In the case of the sixth embodiment shown in FIG. 9, the upper end section of the mirror member 11 is swingably supported by the side wall 30 of the frame section 6 of the lighting device 5 so that the mirror member 11 can be swung up and down. In the case of the seventh embodiment shown in FIG. 10, the central section of the mirror member 11 is swingably supported by the side wall 30 of the frame section 6 so that the mirror member 11 can be turned.

In these sixth and seventh embodiments, the mirror surface 12 is perpendicular to the optical axis L in the mirror use posture M and parallel in the mirror non-use posture L.

Figure 11:
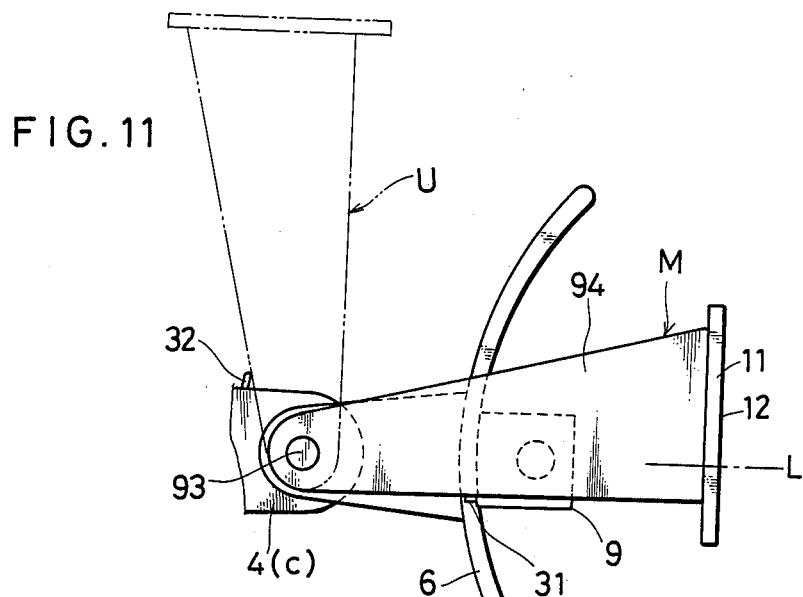
FIG. 11 is a side view of the main section of the eighth embodiment.

FIG. 11 shows the eighth embodiment. In the case of this embodiment, the mirror member 11 is swingably supported by a shaft 93 and a bracket 94 installed on the swivel arm 4 of the lighting device components C, which are used to support the frame section 6, so that the mirror member 11 can be swung up and down. On the side end of the frame section 6, a mirror member support section 31 is disposed so that the mirror surface 12 is perpendicular to the optical axis L when the mirror support section 31 supports the bracket 94. On the upper surface of the swivel arm 4, a stop member 32 is disposed to support the mirror member 11 in the mirror non-use posture U when the mirror member 11 is moved away from the lighting area.

In the case of the lighting device having the reflection plate 7 disposed horizontally, although this type is not shown, the mirror member 11 can be swingably supported in a horizontal plane by a connection arm 4a of the frame section 6 so that the mirror member 11 can have the two switchable postures: the mirror use posture M where the mirror member 11 is positioned in the lighting area and the mirror non-use posture U where the mirror member 11 is moved away from the lighting area.

Figure 12:
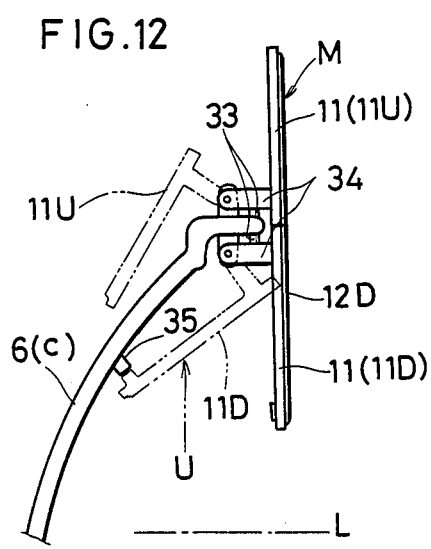
FIG. 12 is a side view of the main section of the ninth embodiment.

FIG. 12 shows the ninth embodiment. In the case of this embodiment, the upper-half piece 11U and the lower-half piece 11D of the mirror member 11 are disposed at the upper end section of the frame section 6. By pivotably supporting the upper-half piece 11U and the lower-half piece 11D at the frame section 6, the mirror member 11 can have the two switchable postures: the mirror use posture M and the mirror non-use posture U. In the mirror non-use posture U of the mirror surface 12D of the lower-half piece 11D can function as a part of the reflection plate. Numeral 33 in FIG. 12 designates posture holding members used to hold the mirror member 11 in the mirror use posture M where the mirror member 11 is perpendicular to the optical axis L of the lighting device 5. The posture holding members 33 are magnets disposed on the upper and lower surfaces of the frame section 6 and attract support arms 34, made of magnetic material, of the mirror member 11. Numeral 35 designates a posture holding device used to hold the lower-half piece 11D at the frame section 6 in the mirror non-use posture U. This posture holding device 35 is also made of magnet.

Figure 13:
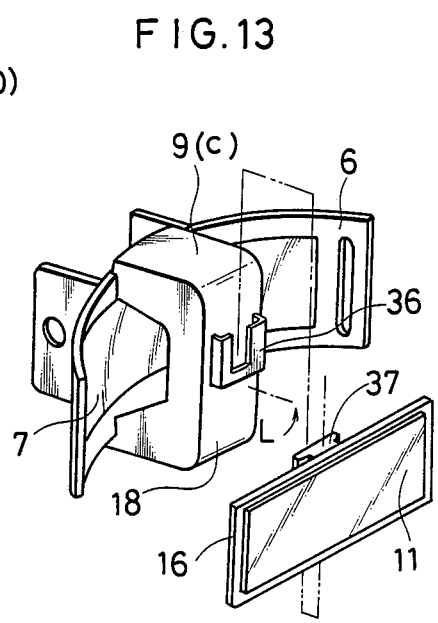
FIG. 13 is a perspective view of the tenth embodiment.

FIG. 13 shows the tenth embodiment, a modification of the present invention. In the case of this embodiment, an accommodation member 36 is disposed on the front 18 of the light source cover 9 to receive the mirror member 11, and an insertion section 37 is disposed on the rear of the frame section 6 of the mirror member 11 so that the mirror member 11 can be installed in and removed from the frame section 6. The mirror surface 12 is perpendicular to the optical axis L of the lighting device 5 when the mirror member 11 is installed in the frame section 6. In the embodiments described above, the mirror surface 12 comprises the ordinary mirror 13 and the semitransparent mirrors 14. However, the entire mirror surface can comprise an ordinary mirror. In this case, the amount of light from the lighting device 5 should be adjustable so that the light of the lighting device 5 can be dimmed when the mirror member 11 is set in the mirror use posture M while the lighting device 5 is lit.

If the greater part of the mirror surface 12 is positioned above the central optical axis in the same way as described in the case of the first embodiment when the mirror member 5 is set in the mirror use posture M, the inside of the mouth can be easily looked at and the lighting efficiency of the lighting device 5 is not reduced.

Instead of the plane mirror used for the mirror member 11 of each embodiment described above, a mirror with a slightly curved surface can be used. With the dental lighting device of the first invention which casts reflected light to the inside of the mouth, the mirror member is mountable on the lighting device and the lighting device components support the mirror member so that the mirror surface of the mirror member is almost perpendicular to the light beam from the reflection plate at least when the mirror member is used. Therefore, both hands of the patient and those of the dentist can be left free when the mirror is used. In addition, since the relationship between the mirror surface and the light beam is fixed at all times, the lighting device can be easily positioned. As a result, both the dentist and the patient can have less burden when the patient looks at the inside of his mouth using the mirror while the dentist instructs the patient how to mount false teeth, for example. Less time is required to look at the inside of the mouth, greatly increasing the working efficiency of the dental chair.

With the dental lighting device of the second invention which supports the mirror member so that the mirror member can have two switchable postures, simply by selecting the mirror use posture, the mirror member can be set at the position where the patient can easily look at the inside of his mouth when the dentist instructs how to mount false teeth or how to brush teeth while the irradiation light is cast into the mouth.

What is claimed:

1. A dental lighting device including a lighting device component composed of a lighting section having a light source and reflection plate, and a lighting support section which adjustably supports said lighting section, wherein the light from said light source is cast into the mouth of a patient via said reflection plate, said lighting device being characterized in that said device comprises a mirror member in combination with said lighting device component to allow the patient to look at the inside of his mouth so that said mirror member can have a mirror use posture where the surface of said mirror member is almost perpendicular to the light beam from said reflection plate at least when said mirror member is used, the mirror member is positioned in front of said lighting section having said reflection plate and a great part of said mirror member is positioned at the upper-half section of said reflection plate when said mirror member is in said mirror use posture.

2. A dental lighting device according to claim 1, wherein said lighting device component used to support said mirror member in said mirror use posture is a frame member used to support said reflection plate.

3. A dental lighting device according to claim 1, wherein said lighting device component used to support said mirror member in said mirror use posture is a light source cover used to cover the front of a light source lamp.

4. A dental lighting device according to claim I, wherein said lighting device component used to support said mirror member in said mirror use posture is the arm of said lighting support section.

5. A dental lighting device including a lighting device component composed of a lighting section having a light source and a reflection plate, and a lighting support section which adjustably supports said lighting section, wherein the light from said light source is cast into the mouth of a patient via said reflection plate, said lighting device being characterized in that said device comprises a mirror member in combination with said lighting device component to allow the patient to look at the inside of his mouth so that said mirror member can have two switchable postures, one of which being a mirror use posture where the surface of said mirror member is almost perpendicular to the light beam from said reflection plate at least when said mirror member is used, and the other being a mirror non-use posture where the surface of said mirror member does not intercept said light beam when said mirror member is not used and a great part of said mirror member is positioned at the upper-half section of said reflection plate when said mirror member is in said mirror use posture.

6. A dental lighting device according to claim 5, wherein said mirror member is supported on the side wall of a cover of said light source so that said mirror member can be swung up and down and so that said mirror member is held above said light source cover in said mirror non-use posture.

7. A dental lighting device according to claim 6, further comprising a cover which is supported over the top of said light source cover so that the surface of said mirror member is covered by said cover when said mirror member is in said mirror non-use posture.

8. A dental lighting device according to claim 5, 6 or 7, wherein the left and right portions of said mirror member surface comprise semi-transparent mirrors.

* * * * *